US00PP10249P

United States Patent [19]

Saville

[11] Patent Number: Plant 10,249

[45] Date of Patent: Feb. 24, 1998

[54] MINIATURE ROSE PLANT NAMED 'SAVAHOLD'

[75] Inventor: F. Harmon Saville, Newburyport, Mass.

[73] Assignee: Nor'East Miniature Roses, Inc., Rowley, Mass.

[21] Appl. No.: 743,517

[22] Filed: Nov. 4, 1996

[51] Int. Cl.[6] ..... A01H 5/00

[52] U.S. Cl. ..... Plt./8.2

[58] Field of Search ..... Plt./8.2

*Primary Examiner*—Howard J. Locker

*Attorney, Agent, or Firm*—Christie, Parker & Hale, LLP

[57] ABSTRACT

A new miniature rose with deep yellow flowers.

1 Drawing Sheet

BACKGROUND OF THE INVENTION

The present invention relates to a new and distinct variety of rose plant of the miniature rose class, which was created by crossing as seed parent an unnamed, undistributed seedling as pollen parent another unnamed, undisseminated seedling of the same parentage. The varietal denomination of this new rose is 'Savahold'.

SUMMARY OF THE INVENTION

Among the novel characteristics possessed by this new variety which distinguishes it from its parents and all other varieties of which I am aware are its attractive deep yellow flowers borne on a plant with abundant dark green foliage.

Asexual reproduction by propagation of vegetative cuttings of the new variety as performed in Essex County, Mass. shows that the foregoing and other distinguishing characteristics come true to form and are established and transmitted through succeeding propagations.

BRIEF DESCRIPTION OF ILLUSRATION

The accompanying illustration shows typical specimens of the flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

Parentage:

*Seed parent.*—Seedling.

*Pollen parent.*—Seedling.

Class: Miniature.

The following observations are made of specimens grown under plastic in Essex County, Mass., during June.

Flower

Blooming habit: Continuous.

A. Bud:

(1) *Size.*—Medium.

(2) *Form.*—Oval with pointed tip becoming urn shaped as petals begin to unfurl.

(3) *Color.*—As sepals divide, bud color is near 12A.

(4) *Sepals.*—Slightly bearded; lanceolate about ⅜-inch longer than the bud; color near 144A; spread to horizontal then drop off with last petals or if hip forms, gradually folds back parallel to stem until hip is mature then turn brown and drop off.

(5) *Pedundle.*—Length — about 13/16 inch. Aspect — straight. Strength — erect. Color — near 146B overlaid with near 177C where exposed to sun.

B. Bloom:

(1) *Size.*—Average size when fully expanded up to about 2 inches.

(2) *Borne.*—Singly and in sprays.

(3) *Form.*—High centered becoming loosely rolled outward.

(4) *Petalage.*—Number of petals under normal conditions about 14–19.

(5) *Color.*—During first two days, inner petals at center of flower are near 12A, reverse is near 13A; outer petals near 12A at base and near 7C at outer edges; reverse near 6D; base petals at point of attachment near 12A; general tonality from a distance bright yellow.

(6) *Color change.*—As bloom ages, color changes from near 12A to near 12A at center and near 12C at outer edges and then to near 12A in center and near 7C at edges, subsequently to near 6B at center and near 4D at edges and finally to all near 4D. After three or more days general tonality is combination of deep yellow and light yellow coloration.

C. Petals:

(1) *Texture.*—Thick.

(2) *Appearance.*—Inside and outside satiny.

(3) *Form.*—Broad fan shaped, petal edges reflexing to points.

(4) *Arrangement.*—Imbricated, reqularly arranged, shingle-like.

(5) *Petaloids in center.*—0–2.

(6) *Persistance.*—Drop off cleanly in 4–5 days.

(7) *Fragrance.*—Slight.

(8) *Lasting quality.*—About 3–5 days on the plant; about 5–7 days as a cut flower.

Reproductive Organs

A. Stamens, filaments and anthers:

*Arrangement.*—In a line on outer edge of receptacle.

B. Stamens:

*Quantity.*—Slightly less than average.

C. Filaments:
*Approximate length.*—Uneven in length.
*General color.*—Near 13A.
D. Anthers:
*Color.*—Near 14C.
E. Pollen:
*Color.*—Near 17A.
*Quantity.*—Small amount.
F. Pistils:
*Quantity.*—Abundant.
G. Styles: Uneven, thin.
*Color.*—Near 1C.
H. Stigmas:
*Color.*—Near 154C.
I. Hips:
*Shape.*—Globular.
*Size.*—Up to about 13/16 to 1 inch in diameter.
*Seeds.*—Seeds do not protrude.
*Color.*—Near 33B.

Plant

A. Form: Upright and compact.
B. Growth: Vigorous, uniform branching.
*Height.*—About 22 to 26 inches.
*Length of flowering stem.*—Varing in length, when borne singly averaging about 9–10 inches.
C. Foliage: Compound of 5–7 leaflets.
*Size.*—Medium.
*Quantity.*—Abundant.
*Color.*—New Foliage: Upper side near 146A; under side near 146B. Old Foliage: Upper side near 147A; under side near 147B.
*Shape.*—Oval, pointed.
*Texture.*—Upper side matte; underside matte.
*Thorns or prickles.*—Usually up to about 4 prickles on underside of leaf stem.
*Edge.*—Serrated.
*Serration.*—Fine, even.
*Leaf stem.*—New — near 176B, underside near 146C; old-top near 147A, underside near 146B.
*Stipules.*—Very finely serrated.
*Resistance to diseases.*—Blackspot: Average. Mildew: Average. Rust: Average.
D. Wood:
*New wood.*—Color near 146B; bark smooth.
*Old wood.*—Color between near 197A and near 147B; bark smooth.
E. Thorns:
*Quantity.*—Few on main stalk and laterals.
*Form.*—Most curve down, occasionally straight.
*Length.*—Less than about ¼ inch.
*Color.*—Near 174C.
*Position.*—Irregular.
F. Prickles:
*Main stalk.*—None.
*Laterals.*—None.
*Leaves.*—Usually about 4 prickles on underside at leaf stems.
G. Winter hardiness: Needs protection in severe climate.

I claim:

1. A new and distinct variety of rose plant of the miniature rose class, substantially as shown and described.

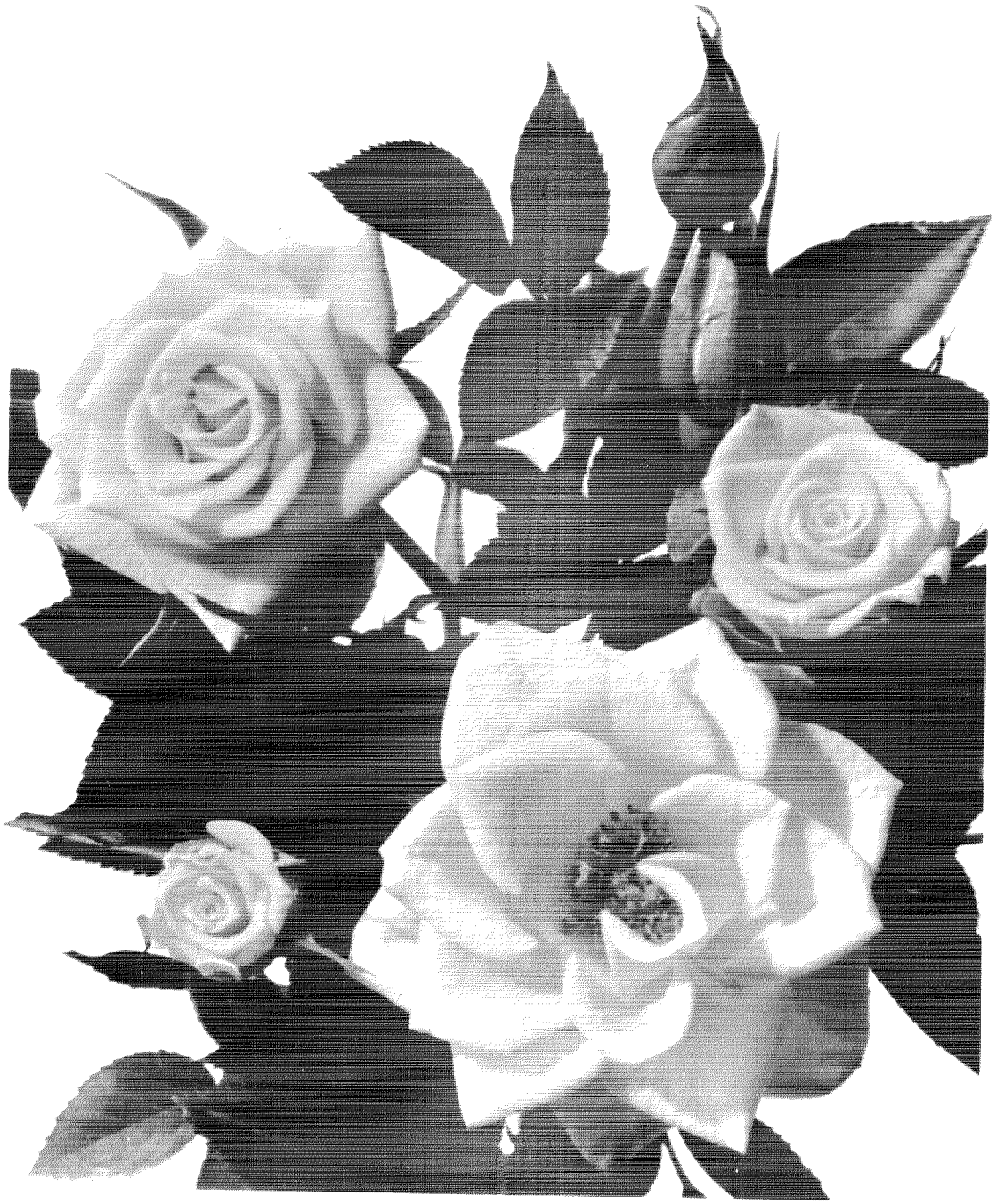

* * * * *